(12) United States Patent
Faccioli et al.

(10) Patent No.: US 9,198,759 B2
(45) Date of Patent: *Dec. 1, 2015

(54) MODULAR SPACER DEVICE FOR THE TREATMENT OF INFECTIONS OF PROSTHESIS OF HUMAN LIMBS

(75) Inventors: Giovanni Faccioli, Monzambano (IT); Renzo Soffiatti, Nogara (IT)

(73) Assignee: TECRES S.P.A., Sommacampagna (Verona) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/236,122

(22) Filed: Sep. 19, 2011

(65) Prior Publication Data

US 2013/0072896 A1   Mar. 21, 2013

(51) Int. Cl.
*A61F 2/32* (2006.01)
*A61F 2/30* (2006.01)
*A61F 2/36* (2006.01)

(52) U.S. Cl.
CPC ... *A61F 2/32* (2013.01); *A61F 2/36* (2013.01); *A61F 2/3609* (2013.01); *A61F 2002/3055* (2013.01); *A61F 2002/3092* (2013.01); *A61F 2002/30405* (2013.01); *A61F 2002/30448* (2013.01); *A61F 2002/30449* (2013.01); *A61F 2002/30616* (2013.01); *A61F 2002/30617* (2013.01); *A61F 2002/30672* (2013.01); *A61F 2002/30677* (2013.01); *A61F 2002/30733* (2013.01); *A61F 2002/365* (2013.01); *A61F 2310/00353* (2013.01); *A61F 2310/00952* (2013.01)

(58) Field of Classification Search
CPC ............. A61F 2/32; A61F 2002/3631; A61F 2002/3633; A61F 2002/365; A61F 2/36
USPC .................................. 623/22.11, 18.11, 23.29
See application file for complete search history.

(56) References Cited

U.S. PATENT DOCUMENTS 3,987,499 A * 10/1976 Scharbach et al. ......... 623/17.11
7,601,176 B2 * 10/2009 Soffiati et al. .............. 623/18.11

FOREIGN PATENT DOCUMENTS

| EP | 1274374 | 1/2003 |
| EP | 1 274 374 B1 | 12/2008 |
| WO | 2007/099232 A2 | 9/2007 |
| WO | WO2007099232 | 9/2007 |

OTHER PUBLICATIONS

WO 2010/015877, Faccioi et al, filed Feb. 11, 2010.*

* cited by examiner

*Primary Examiner* — Bruce E Snow
(74) *Attorney, Agent, or Firm* — Tutunjian & Bitetto, P.C.

(57) ABSTRACT

A spacer device for the two-stage treatment of infections of the prosthesis of the human limbs, made of biologically compatible material adapted to be added and/or which can be added with pharmaceutical products, active and/or therapeutic ingredients, includes a first portion adapted to be fixed to a corresponding bone bed, and a second portion adapted to be inserted in a corresponding articular area of the patient, said first portion and said second portion being connected through adjustable joining means. The device includes mutual coupling surfaces respectively provided in said first portion and said second portion coated with said biologically compatible material. A method for locking the first portion to the second portion is also provided.

20 Claims, 3 Drawing Sheets

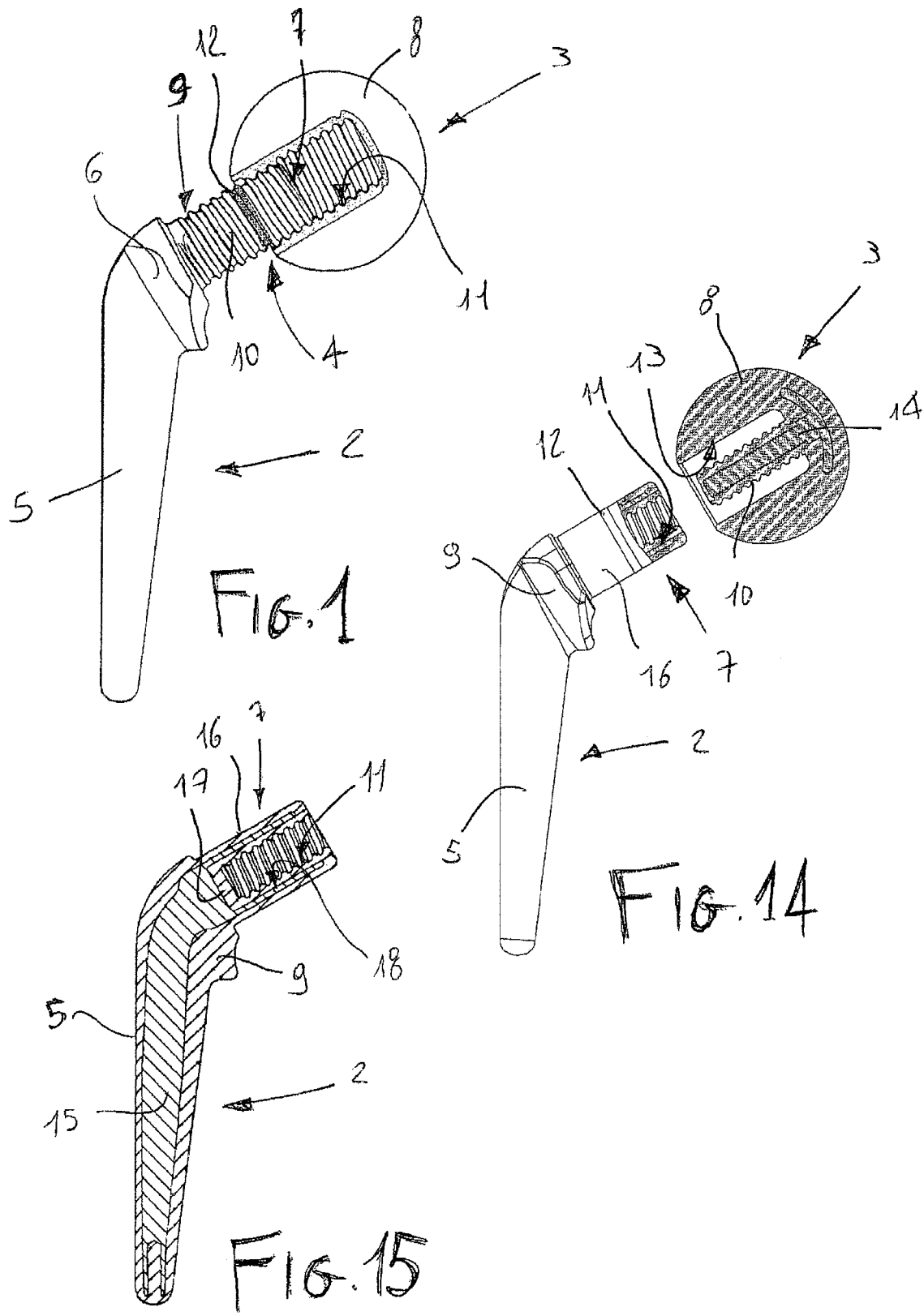

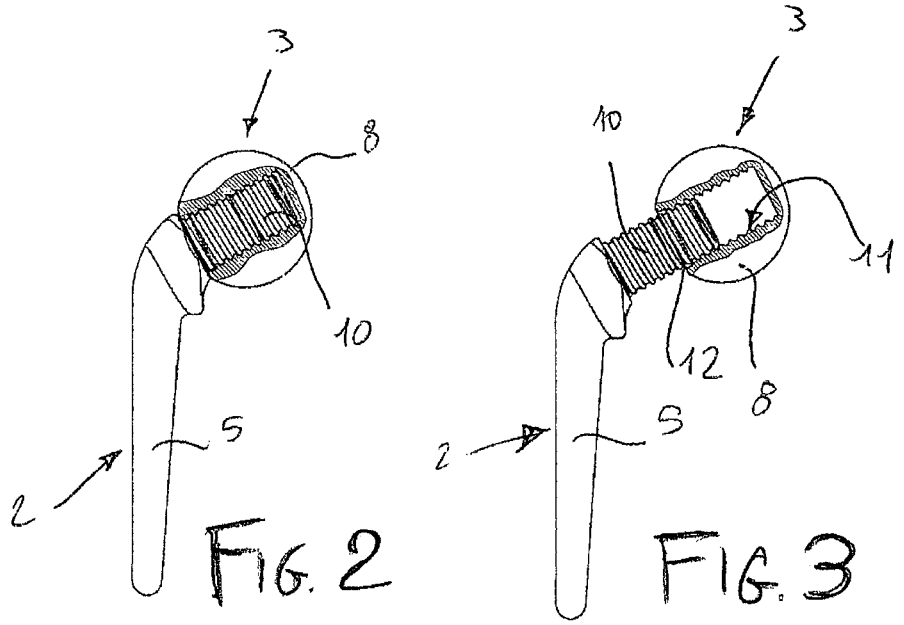
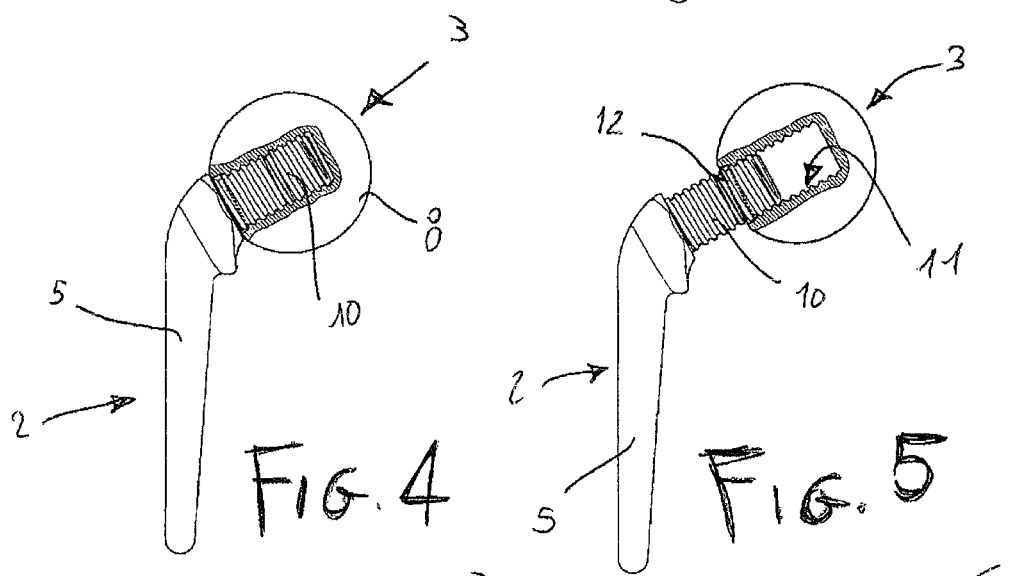
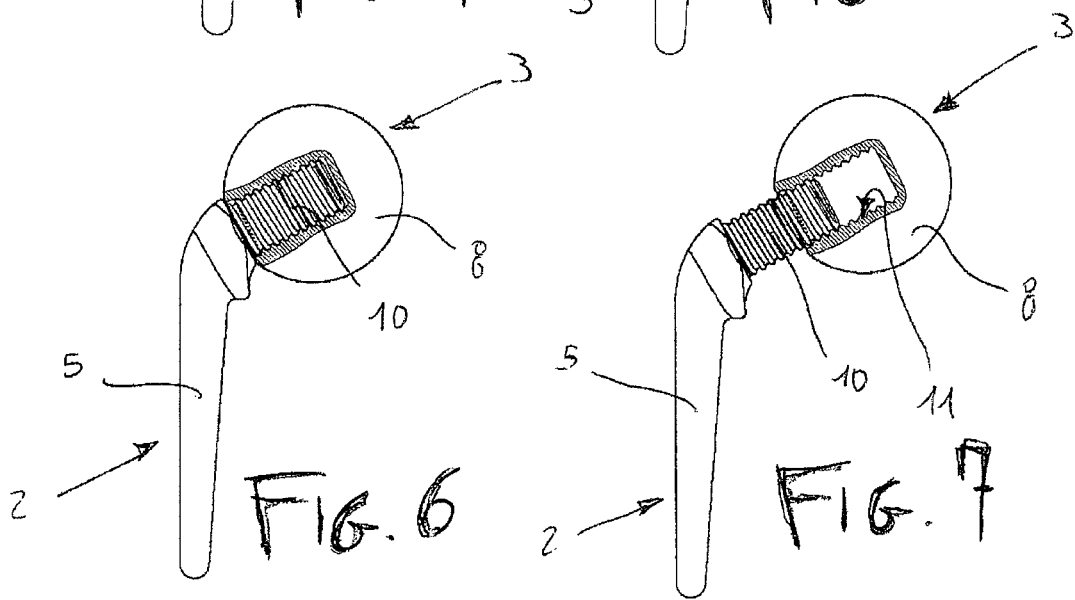

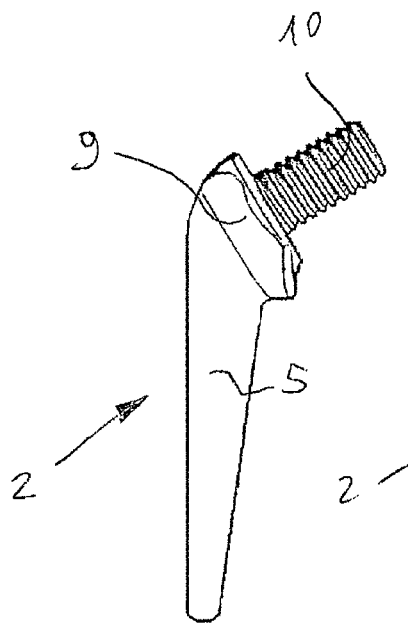
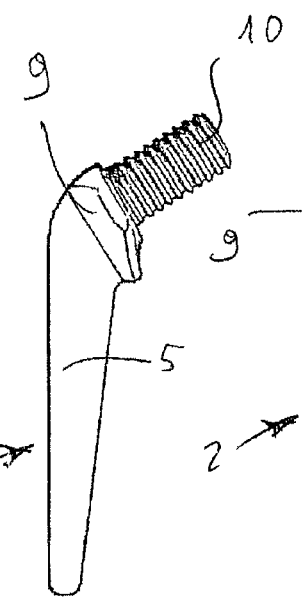
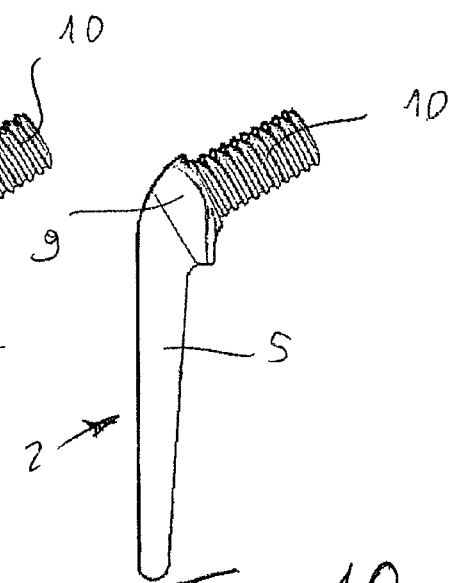
FIG. 8   FIG. 9   FIG. 10
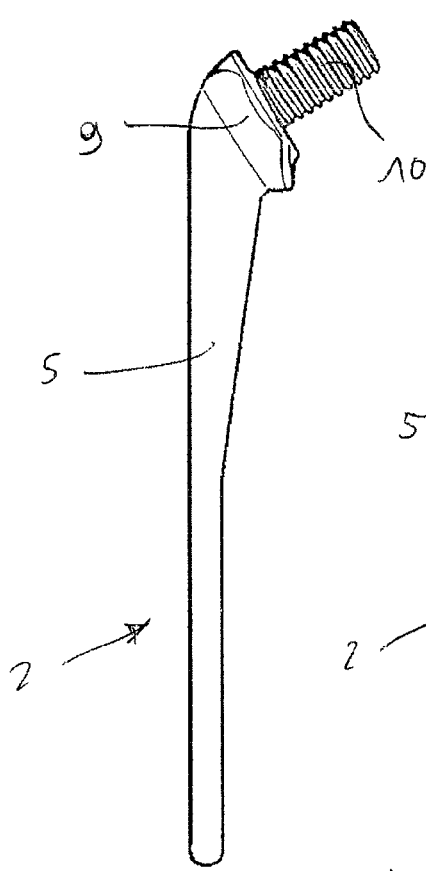
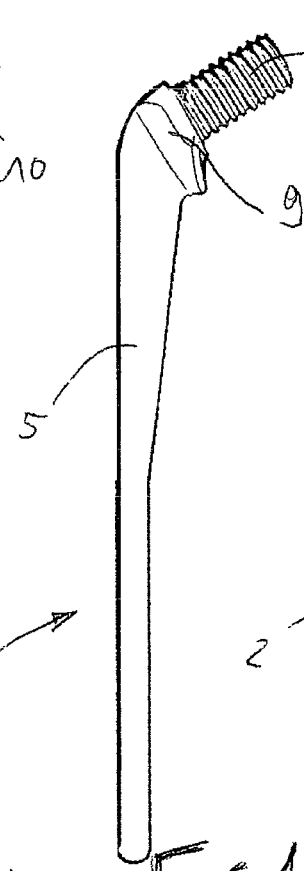
FIG. 11   FIG. 12   FIG. 13

MODULAR SPACER DEVICE FOR THE TREATMENT OF INFECTIONS OF PROSTHESIS OF HUMAN LIMBS

BACKGROUND

1. Technical Field of the Invention

The present invention regards a spacer device for the two-stage treatment of arthroprosthesis infections, for example hip prostheses, humeral prostheses, knee prostheses, ankle prostheses, etcetera.

2. Description of Related Art

Arthroprosthesis infections are among the most serious causes of failure of an arthroprosthesis. With specific reference to hip arthroprostheses, such events occur quite often with a percentage variable between 0.5% and 6% of the cases. The percentage of negative events increases in cases of re-implantation or in presence of risk factors such as previous interventions, local haematoma, intercurrent infectious diseases, local or general bone diseases, immunosuppression, etcetera.

A method for curing the infection, defined a two-stage treatment, provides for a first stage of removing the infected arthroprosthesis, the possibilities of success of the conservative antibiotic treatment are actually quite limited, and a second stage of a new re-implant of arthroprosthesis upon clearing the tissues of the patient in terms of infection.

In order to maintain the space required for the new re-implantation of arthroprosthesis and cure the infection, the applicant developed special arthroprostheses for temporary use, also referred to as spacers or temporary spacers, which release pharmaceutical and/or therapeutic products and allow articular mobility.

The aforementioned spacers are disclosed by the Italian patent No. IT-1278853 and European patent No. EP-1274374 on behalf of the applicant, the contents of which are incorporated herein by reference.

The International patent application WO-2007/099232 discloses a temporary spacer comprising a semispherical head to be inserted in the corresponding articulation separable and connectable to a stem to be inserted in the bone bed remaining from a previous implant. The spacer illustrated in WO-2007/099232 allows combining a stem with semispherical heads of different sizes so as to best adapt to the anatomy of the articulation of the patient.

There arises the need of providing a solution alternative to the known ones, in particular more efficient, safe and inexpensive as regards the mutual locking between the stem and the head.

SUMMARY OF THE INVENTION

An object of the present invention is to improve the prior art.

Another object of the present invention is to obtain a spacer device that can be easily adapted to the different sizes of the patients.

Still another object of the present invention is to obtain a spacer device that is more efficient, safe and inexpensive as regards the operation of mutual locking between the stem and the head.

A further object of the present invention is to provide a spacer device that allows maintaining the articular functionality reducing the recovery times for the patient.

Still another object of the present invention is to provide a spacer device capable of also bearing dynamic loads, at least for a given period of time, awaiting the final re-implant.

According to an aspect of the invention a spacer device is provided.

BRIEF DESCRIPTION OF THE DRAWINGS

Further characteristics and advantages of the present invention will be more apparent from the description of some embodiments of the present invention, illustrated by way of example in the attached drawings wherein:

FIG. 1 is a lateral view, partly sectioned, of a spacer device according to an aspect of the present invention;

FIG. 2 is a lateral view, partly sectioned, of a spacer device according to an aspect of the present invention constituted by the coupling of a normal stem and by a small-sized sphere, entirely fastened;

FIG. 3 is a lateral view, partly sectioned, of a spacer device according to an aspect of the present invention constituted by the coupling of a normal stem and by a small-sized sphere, entirely unfastened;

FIG. 4 is a lateral view, partly sectioned, of a spacer device according to an aspect of the present invention constituted by the coupling of a normal stem and by a medium-sized sphere, entirely fastened;

FIG. 5 is a lateral view, partly sectioned, of a spacer device according to an aspect of the present invention constituted by the coupling of a normal stem and by a medium-sized sphere, entirely unfastened;

FIG. 6 is a lateral view, partly sectioned, of a spacer device according to an aspect of the present invention constituted by the coupling of a normal stem and by a large-sized sphere, entirely fastened;

FIG. 7 is a lateral view, partly sectioned, of a spacer device according to an aspect of the present invention constituted by the coupling of a normal stem and by a large-sized sphere, entirely unfastened;

FIGS. 8,9,10 are lateral views of different embodiments of the stem, normal-sized, of the spacer device according to an aspect of the present invention;

FIGS. 11,12,13 are lateral views of different embodiments of the stem, long-sized, of the spacer device according to an aspect of the present invention;

FIG. 14 is a lateral view, partly sectioned of another embodiment of the spacer device according to an aspect of the present invention;

FIG. 15 is a lateral sectioned view of the stem of the spacer device of FIG. 14.

DETAILED DESCRIPTION OF PREFERRED EMBODIMENTS

With reference to the figures, a spacer device according to the present invention, in particular a spacer device for the two-stage treatment of infections of the prosthesis of the human limbs is indicated in its entirety with 1.

In the illustrated embodiment express reference shall be made to a spacer for the treatment and the replacement of hip arthroprosthesis, even though it should be observed that the present invention can be used also for treating other types of prostheses, for example, humeral prostheses, knee prostheses, ankle prostheses etcetera.

The device 1 according to the present invention is made of biologically compatible material, it can be porous and it is adapted to be added and/or it can be added with one or more pharmaceutical products, active and/or therapeutic ingredients adapted to be released in the tissues of the patient adjacent to the device. The materials for the spacer device according to the present invention can be selected from among metals, metal alloys, organic metals, ceramic, glass, plastic. Specifically the plastic can be selected from among thermoplastic polymers, such as acrylic resins, including all copolymers and acrylic alloys, polyethylene, polypropylene thermoformable through injection moulding or through blow moulding.

In a version of the invention, the biologically compatible material with which the spacer device is made comprises polymethylmethacrylate.

The material the spacer device according to an aspect of the present invention is made of may already comprise one or a plurality of first pharmaceutical products, active and/or therapeutic ingredients, for example antibiotics, and also being porous it further can be added and/or imparted, for example by impregnation, with one or more pharmaceutical products, active and/or therapeutic ingredients identical or different with respect to the first pharmaceutical products, active and/or therapeutic ingredients.

In a further version of the invention, the spacer does not comprise pharmaceutical products, active and/or therapeutic ingredients and is added and/or imparted, for example by impregnation, with one or more pharmaceutical products, active and/or therapeutic ingredients when implanting in the patient.

Thus, at least three different types of spacer materials can be used in terms of the pharmaceutical and therapeutic products:

material already comprising one or a plurality of pharmaceutical products, active and/or therapeutic ingredients, without the possibility of adding other pharmaceutical and/or therapeutic products;

material already comprising one or a plurality of pharmaceutical products, active and/or therapeutic ingredients with the possibility of adding other pharmaceutical and/or therapeutic products, for example by impregnation when the material is porous;

material not comprising any pharmaceutical product, active and/or therapeutic ingredient, with the possibility of adding one or a plurality of pharmaceutical products, active and/or therapeutic ingredients, when implanting in the patient, for example by impregnation, when the material is porous. The pharmaceutical products, active and/or therapeutic ingredients may comprise antibiotics, antiseptics, antimycotics, chemotherapeutic substances, for example gentamicin, vancomycin, etcetera, or other active ingredients.

According to the figures, the device 1 comprises a first portion 2 adapted to be fixed to a corresponding residue bone bed of a previous implant, a second portion 3 adapted to be inserted in a corresponding articular area of the patient.

The first portion 2 and the second portion 2 are connected through joining means, indicated in their entirety with 4, which are of the adjustable type. In addition, they are provided with the locking means adapted to fix the position of the adjustable joining means 4, better described hereinafter.

In the embodiment versions of the figures, which regard the articulation of the hip, the first portion 2 comprises a stem 5 to be inserted in the proximal part of a femur.

The first portion 2 is provided with an inner reinforcement core, for example made of metal material or any other material having suitable mechanical characteristics.

The stem 5 is substantially frusto-conical shaped and also comprises a widened portion 6, proximal to the end 7 for connection to the second portion 3.

The second portion 3 of the device according to the invention comprises a substantially spherical head 8.

Heads 8 with different dimensions, in particular with different diameter of the sphere so as to be adapted to the different sizes of the articular capsules of the patients can be provided for like those illustrated for example in FIGS. 2-7.

For example, in FIGS. 2,3 there is illustrated an embodiment of the spacer device comprising a head 8 that is small in size, respectively entirely fastened to or entirely unfastened from first portion 2.

In FIGS. 4, 5 there is illustrated an embodiment of the spacer device comprising a head 8 that is medium-sized, respectively entirely fastened to or entirely unfastened from the first portion 2.

In FIGS. 6, 7 there is illustrated an embodiment of the spacer device comprising a head 8 that is large-sized, respectively entirely fastened to or entirely unfastened from the first portion 2.

FIGS. 2-7, thus illustrate some of the possible combinations between the same first portion 2 of the spacer device with second portions 3 comprising variously sized heads 8, depending on the specific application needs, i.e., for an improved adaptation to the anatomy of the patient.

An important characteristic of the spacer device according to the present invention is constituted by the adjustable joining means 4 which, besides the function of connecting the first portion 2 and the second portion 3, also allow adjusting the mutual position between the first portion 2 and the second portion 3. In the embodiment of the figures, due to the adjustable joining means 4, it is possible to vary the length of the neck 9 of the device 1, once again for better adaptation to the anatomy of the patient on which the device is implanted.

According to an aspect of the present invention, the joining means 4 comprise mutual coupling surfaces 10,11 respectively provided in the first portion 2 and in the second portion 3.

The mutual coupling surfaces 10,11 are both coated with the biologically compatible material.

In other words, the mutual coupling surfaces 10,11 are coated with the same material with which the remaining parts of the first portion 2 and of the second portion 3 of the spacer device 1 are made. The advantages of this solution will be clear hereinafter.

The aforementioned mutual coupling surfaces 10,11 comprise, more in detail, a screw 10 and a nut screw 11.

The screw 10 and the nut screw 11 are of the type having a threading with rounded profile.

For example, for better understanding, it should be observed that such profile is substantially similar to the combined profile of Edison type, or other similar profiles.

This solution allows obtaining a greater breaking strength and an improved capacity of the threads to be moulded in the production stage, and also other advantages to be better clarified in the description hereinafter.

Thus, there can also be provided profiles with greater pitch, so as to increase the coupling surfaces and thus increase the resistance of the coupling. In the embodiments of FIGS. 1-13, the screw 10 is provided in the first portion 2 of the device, i.e. it is obtained at the end 7 of the stem 5.

The nut screw 11 is instead provided in the second portion 3, i.e., it is comprised in the sphere 8.

According to another aspect of the present invention, the first portion 2 of the spacer device comprises a visual indicator 12 of the position of complete unfastening of the second portion 3 with respect to the first portion 2.

Such visual indicator 12, in other words, allows identifying, along the thread of the screw 10, the limit position beyond which the second portion 3 should never be unfastened so as not to jeopardize the stability of the coupling between the two portions 2,3. More particularly, the visual indicator 12 comprises a band made along the outer surface of the screw 10.

The band of the visual indicator 12 may be obtained, for example, using a special paint, or any other type of pigment, whose colour is clearly visible to the operator in any situation, or through other equivalent techniques.

As mentioned, FIGS. 2-7 show various combinations of couplings between the same first portion 2 and different second portions 3, i.e. in particular between the same stem 5, normal-sized, and heads 8 of various sizes. In particular, FIGS. 2,4,6 illustrate the device with the head 8 entirely fastened to the respective stem 5, while FIGS. 3,5,7 illustrate the device with the head 8 entirely unfastened, i.e., unfastened until it moves to the visual indicator 12.

Obviously, such positions represent the limit adjustment positions: the device can be adjusted in any intermediate position between the aforementioned limit positions.

It is thus clear that numerous combinations, regarding the sizes of the first portion 2, the sizes of the second portion 3 and the obtainable length of the neck 9 of the device 1 can be obtained, so as to meet any application requirement.

FIGS. 8-13 further illustrate different embodiments of the first portion 2 of the device according to the invention.

More particularly, FIGS. 8-13 regard stems 5 of different shapes and sizes.

FIGS. 8-10 regard stems 5 of normal sizes provided with widened portions 6 of different dimensions, for a better adaptation to the anatomic characteristics of the patients.

In FIGS. 11-13, instead, there are represented long-sized stems 5 provided with widened portions 6 of different sizes, still for a better adaptation to the anatomic characteristics of the patients.

According to an aspect of the present invention the means for locking the first portion 2 to the second portion 3, in the desired position required by the specific application, comprise portions of the aforementioned coupling surfaces 10,11 rigidly welded by applying a bonding component.

As clarified hereinafter, in a version of the present invention, the bonding component, applied and left to act for a given period of time, provides for dissolving the surface layers of the biologically compatible material of the coupling surfaces 10,11 and then facilitating the subsequent mutual welding once brought to contact.

Regarding this, described hereinafter is a method per the mutual locking of the first portion 2 to the second portion 3 of the spacer device according to the invention in the desired position, depending on the specific application requirements.

The method initially provides for a stage of distributing a predefined amount of bonding component on at least one of the coupling surfaces 10,11, which as mentioned are made of biologically compatible material comprising polymethylmethacrylate.

The bonding component can be of different type. For example, acrylic bone cement, or a cyanoacrylate bonding agent, or even an organic solvent or a mixture of several components, such as chloroform, methyl methacrylate, ethyl acetate, dichloromethane and many others can be used.

Obviously, any component that is used should be stable and biocompatible.

Such stage of distributing the bonding component is performed, in particular, by filling the nut screw 11 of the second portion 3 with the bonding component. The bonding component can be made available for example in a special vial, which is opened at the moment of use.

Subsequently there is provided a stage for applying a closure cap to the nut screw 11, so as not to disperse the bonding component.

The closure cap is small in size, in particular short, so as not to obstruct the first threads of the nut screw 11.

The two parts can be subsequently immediately coupled, but it is preferable to provide for a stage of waiting for a given period of time, for example about one minute, to allow the bonding agent to act and complete the effect thereof on polymethylmethacrylate. Once such period of time has elapsed, the closure cap is removed and the coupling surfaces 10,11—screw and nut screw—of the first portion 2 and of the second portion 3, are joined in the desired position.

In more detail, the head 8 is fastened to the screw 10 up to the desired position, so as to obtain a neck 9 of the desired length.

Lastly, there is provided a stage of waiting for a further predefined period of time to allow the mutual stable fixing of the coupling surfaces 10,11; in such stage the device should not be subjected to movements so as not to lose the mutual positioning of the first portion 2 and of the second portion 3.

Such predefined period of time can be, for example, about one hour or at least one hour.

Thus, over this period of time the surface layers of the coupling surfaces 10,11 of the first portion 2 and of the second portion 3 are mutually welded, obtaining a fixing that is rigid, resistant and safe over time.

As evincible from the previous description, locking the first portion 2 to the second portion 3 of the spacer device 1 according to the invention can be obtained in a quick, accurate, simple and inexpensive manner, without using specific mechanical locking means or other expensive or complex systems.

Furthermore, it should be observed that both the first portion 2 and the second portion 3 of the spacer device according to the invention are entirely without exposed metal parts: actually, the surfaces thereof are completely coated with biologically compatible material, eliminating the possibility of infections occurring.

Furthermore, there can also be provided other embodiments of the locking method described above, for example providing for other equivalent methods for distributing the bonding component on the coupling surfaces 10, 11. For example, in some embodiments of the method the bonding component can be applied on both coupling surfaces 10, 11 instead of only one.

Another embodiment of the spacer device according to the invention is illustrated in FIGS. 14,15.

This embodiment differs from the previous one due to the fact that the positions of the coupling surfaces 10,11 of the first portion 2 and of the second portion 3 are inverted.

In more detail, in this embodiment the screw 10 is provided in the second portion 3, i.e. in the spherical head 8, while the nut screw 11 is provided in the first portion 2, i.e. in the end 7 of the stem 5.

As observed in particular in FIG. 14, the screw 10 is provided within a cylindrical seat 13 provided in the spherical head 8.

In order to confer the required mechanical resistance, the screw 10 is provided with a respective second core 14 incorporated in the head 8.

The core 14 can for example be made of metal material, or any other material having suitable characteristics.

The first portion 2, as described in the previous embodiment comprises a first reinforcement core 15, for example made of metal material or any other material having suitable characteristics.

The first portion 2 comprises, in the present embodiment, an end shank 16 of the stem 5, having a smooth cylindrical outer surface.

The outer diameter of the end shank 16 is such to be inserted in the cylindrical seat 13 with considerable accuracy, without requiring applying force.

The nut screw 11 is obtained, in particular, in a bushing 17 inserted in a respective housing 18 provided in the first core 15 of the first portion 2.

The bushing 17 is made of the same biologically compatible material with which the remaining parts of the first portion 2 are made.

As observable in the section of the FIG. 15, the first core 15 of the first portion 2 is entirely covered by the biologically compatible material. Thus, there are no exposed metal parts also in this embodiment.

Also in this embodiment the biologically compatible material comprises polymethylmethacrylate.

In the present embodiment, the visual indicator 12 comprises a band made along the outer surface of the shank 16 of the stem 5, as illustrated in FIG. 14.

The band of the visual indicator 12 may be obtained according to the criteria described regarding the preceding embodiment.

The second portion 3 is locked to the first portion 2 in a manner entirely similar to the one described regarding the preceding embodiment.

In particular, the stage of distributing a predefined amount of bonding component on at least one of the coupling surfaces 10,11 occurs by filling the nut screw 11 provided in the first portion 2, and then applying a cap thereon.

Then, there follows the stages described regarding the preceding embodiment, obtaining the same results and the same advantages described previously.

The present invention thus conceived can be subjected to various modifications and variants all falling within the scope of protection of the claims.

The invention claimed is:

1. A spacer device for the two-stage treatment of infections of the prosthesis of the human limbs, made of biologically compatible material adapted to be added with one or more of pharmaceutical products, comprising a stem adapted to be fixed to a corresponding bone bed, a head adapted to be inserted in a corresponding articular area of the patient, said stem including a widened portion proximal to an end of the stem for connection to the head, said widened portion being non-flaring with respect to the stem at least at a lateral topside of the widened portion and forming a smooth curvature with said lateral top side of the stem, and said head being connected through adjustable joining means, wherein said joining means comprise mutual coupling surfaces comprising a threaded screw in said stem and a nut screw in said head, wherein said threaded screw is attached directly to said widened portion and the head is capable of adjustment along the threaded screw to directly contact the widened portion and wherein said mutual coupling surfaces are coated with said biologically compatible material adapted to be added with said one or more of pharmaceutical products.

2. The device according to claim 1, wherein said stem is configured to be inserted in the proximal part of a femur.

3. The device according to claim 1, wherein said stem has a size adapted to the size of a femur of a patient.

4. The device according to claim 1, wherein said head comprises a substantially spherical head, said head having a size adapted to the size of an articular capsule of a patient.

5. The device according to claim 1, wherein said screw and nut screw comprise threading with rounded profile.

6. The device according to claim 1, wherein said stem comprises a visual indicator of a position of complete unfastening of said second portion from the first portion.

7. The device according to claim 6, wherein said visual indicator comprises a band made along the outer surface of said screw.

8. The device according to claim 1, wherein said biologically compatible material comprises polymethylmethacrylate.

9. The device according to claim 1, comprising a bonding component adapted to fix the position adjustable joining means and thus the mutual position between said stem and head.

10. The device according to claim 9, wherein said bonding component comprise portions of said mutual coupling surfaces rigidly welded by applying said bonding component.

11. The device according to claim 10, wherein said bonding component comprises at least one of acrylic bone cement, or a cyanoacrylate bonding agent, or an organic solvent or a mixture comprising one or more of chloroform, methyl methacrylate, ethyl acetate, and dichloromethane.

12. The device according to claim 1, wherein said stem is substantially frusto-conical so as to hold the trochanter of the femur on which said stem should be implanted.

13. The device according to claim 1, wherein said biologically compatible material comprises one or more first pharmaceutical products adapted to be released in the tissues of the patient adjacent to the device.

14. The device according to claim 1, wherein said biologically compatible material is porous and can be added by impregnation, with one or more pharmaceutical products.

15. The device according to claim 13, wherein said pharmaceutical products comprise one or more of the following products: antibiotics, including gentamicin, vancomycin, antiseptics, antimycotics, chemotherapeutic substances.

16. The device according to claim 1, wherein said biologically compatible material comprises materials selected from among metals, metal alloys, organic metals, ceramic, glass and plastic.

17. The device according to claim 1, wherein said biologically compatible material comprises a plastic selected from among thermoplastic polymers, acrylic resins, including copolymers and acrylic alloys, polyethylene and polypropylene.

18. The device according to claim 17, wherein said plastic is thermo-formable through injection moulding or through blow moulding.

19. A spacer device for the treatment of infections of the prosthesis of the human limbs, made of biologically compatible material adapted to be added with one or more active ingredients, comprising:
   a first portion comprising a stem adapted to be fixed to a corresponding bone bed; and
   a second portion adapted to be inserted in a corresponding articular area of a patient, said stem including a widened portion proximal to an end of the stem for connection to the second portion, said widened portion being non-flaring with respect to the stem at least at a lateral topside of the widened portion and forming a smooth curvature with said lateral top side of the stem, and said second portion being connected through adjustable joining means, wherein said joining means comprise mutual coupling surfaces comprising a threaded screw in said first portion and a nut screw in said second portion, wherein said threaded screw is attached directly to said widened portion and the head is capable of adjustment along the threaded screw to directly contact the widened portion and wherein both said screw and said nut screw include a coating comprising a biologically compatible and porous material adapted to be added with said one or more active ingredients.

20. A spacer device for the two-stage treatment of infections of the prosthesis of the human limbs, made of biologically compatible material adapted to be added with one or more of pharmaceutical products, comprising a first portion comprising a stem adapted to be fixed to a corresponding bone bed, a second portion adapted to be inserted in a corresponding articular area of the patient, said stem including a widened portion proximal to an end of the stem for connection to the second portion, said widened portion forming a continuous surface flush with a top side of the stem, and said second portion being connected through adjustable joining means, wherein said joining means comprise mutual coupling surfaces comprising a screw in said first portion and a nut screw in said second portion, wherein said mutual coupling surfaces are coated with said biologically compatible material adapted to be added with said one or more of pharmaceutical products, wherein said first portion comprises a visual indicator of a position of complete unfastening of said second portion from the first portion, wherein said visual indicator comprises a band made along the outer surface of said screw.

* * * * *